United States Patent
Berens

Patent Number: 5,998,160
Date of Patent: Dec. 7, 1999

[54] GUIDED CELL SEDIMENTATION FOR BIOLOGICAL STUDIES

[75] Inventor: Michael E. Berens, Gilbert, Ariz.

[73] Assignee: CSM, Inc., Mesa, Ariz.

[21] Appl. No.: 08/975,558

[22] Filed: Nov. 21, 1997

[51] Int. Cl.[6] ....................................................... C12Q 1/24
[52] U.S. Cl. .......................................... 435/30; 435/309.1
[58] Field of Search .................................. 435/30, 31, 32, 435/33, 283.1, 309.1, 309.4; 422/100

[56] References Cited

U.S. PATENT DOCUMENTS

| | | |
|---|---|---|
| 4,912,057 | 3/1990 | Guirgus et al. . |
| 5,514,555 | 5/1996 | Springer et al. . |
| 5,578,492 | 11/1996 | Fedun et al. . |

FOREIGN PATENT DOCUMENTS

001364633 A1  1/1998  U.S.S.R. .............................. 435/309.1

OTHER PUBLICATIONS

Walther, B.T., Öhman, R., and Roseman, S. A quantitative assay for intercellular adhesion. Proc. Natl. Acad. Sci. USA 70(5):1569–1573, 1973.

Zetter, B.R. Migration of capillary endothelid cells is stimulated by tumour–derived factors. Nature 285:41–43, 1980.

Barak, Y., Karov, Y. and Levin, S. Migration of human leukocytes from soft agarose droplet: A simplified Method . . . Amer. J. Hematol. 14:271–278, 1983.

Berens, M.E., Rief, M.D., Loo, M.A. and Giese, A. The role of extracellular matrix in human astrocytoma migration and proliferation . . . Clin. Exp. Metastasis 12:405–415, 1994.

Chicoine, M.R. and Silbergeld, D.L. Assessment of brain tumor cell motility in vivo and in vitro. J. Neurosurg 82:615–622, 1995.

DiMuzio, P.J., Pratt, K.J., Park, P.K., and Carabasi, R.A. Role of thrombin in endotheliol cell monolayer repair in vitro. J. Vasc. Surg. 20:621–628, 1994.

Jungi, T.W. Assay of chemotaxis by a reversible Boyden Chamber eliminating cell detachment. Int. Archs. Allergy Appl. Immun. 48:341–352, 1975.

Miki, I., Ishihara, N., Otoshi, M. and Kase, H. Simple colorimetric cell.cell adhesion assay using MTT–stained leukemia cells. J. Immunol. Methods 164:255–261, 1993.

Milner, R., Anderson, HJ, Rippon, R.F., McKay, JS, Franklin, JM, Marchionni, MA, Reynolds, R. and ffrench. Constant, C. Contrasting effects of mitogenic growth factors . . . Glia 19:85–90, 1997.

Nelson, RD, Quie PG and Simmons, RL. chemotaxis under agarose: a new and simple method for measuring chemotaxis and spontaneous migration . . . J. Immunol. 115(6):1650–1656, 1975.

Rupnick, MA, Stokes, CL., Williams, SK, and Lauffenburger DA. Quantitative analysis of random motility of human microvessel. . . Lab. Investigation 59(3):363–372, 1988.

Phelps P. and Stanislaw D. Polymorphonuclear leukocyte motitity in vitro. I. Effect of pH, temperature, ethyl alcohol and caffein, using a modified Boyden chamber technique. Arthritis and Rheumatism 12(3):181–188, 1969.

Varani, J. Orr, W. and Ward P.A. A comparison of the migration patterns of normal and malignant cells in two assay systems. Am. J. Pathol. 90:159–172, 1978.

*Primary Examiner*—David A. Redding

[57] ABSTRACT

A method whereby living cells are passively deposited onto a flat surface by gravity force through vertical channels so as to establish a disk of cells at a predetermined area and of predetermined size.

8 Claims, 4 Drawing Sheets

GUIDED CELL SEDIMENTATION FOR BIOLOGICAL STUDIES

This work was supported by grant NS 27030 from the National Institute of Neurological Disorders and Stroke of the National Institutes of Health. The United States Government has certain rights to this invention.

BACKGROUND

1. Field of Invention

This invention relates to a method for biology research specifically to such a method that allows replicate samples of living cells to be evenly and reproducibly deposited by gravity sedimentation within a predetermined area.

2. Discussion of Prior Art

A burgeoning field in biology is the study of how cells move. Scientific disciplines applied to the study of cell movement range from developmental biology, neuroscience, immunology, nerve regeneration, cancer cell metastasis, and others. The mechanisms by which cells attach to surfaces, and the responses triggered by those attachments, demonstrate profound control over a cell's behavior through contact with surface molecules. Laboratory techniques which elicit specific, controllable interactions between a cell and external molecules enable advances in understanding the biochemical and genetic basis of these interactions. Conducting studies on cells in response to the external environment requires the placement of cells at specific locations. The state of the art for studies of cell movement response to external molecules is reviewed below.

Attachment assays. The initial interaction of a cell with its extracellular matrix can be studied using an attachment assay (Walther B T et al 1973; Miki I et al 1993). These techniques involve initial coating of a surface with a substrate, typically a protein. Cells are added and allowed to sediment at 4° C. onto the substrate. Once the cells have sedimented, the assay vehicle is moved to 37° C. for physiological attachment. The duration of the adhesion assay may vary according to the cells being studied and the nature of the substrate. After the cells attach, free cells are washed away and the remaining cells are enumerated. This is accomplished using either direct cell counting under a microscope or other indirect measures of cell number. These include counting of cells labeled previously with some radioactive compound, or other calorimetric or fluorescent endpoints indicative of cell number. There is a linear relationship between the measurement and the number of cells by which the fraction of attached cells can be determined. These assays are single endpoint assays of cell adhesion to substrates. Determining the kinetics of attachment requires multiple replicate experiments being analyzed at different times. The mechanism for attachment can be inferred using blocking antibodies that interfere with either certain receptors on the cell surface or that block ligands on the substrate. The state of the art also includes using molecular genetic techniques to alter the levels of expression of genes believed to be involved in cell attachment. Direct studies of morphological changes in the cells, changes in cell growth properties, or evaluation of biochemical and genetic changes by the cells in response to attachment cannot be addressed using these techniques. Additionally, appropriate control conditions in the experiments using mock-manipulated cells are potentially inadequate to properly assess other changes in the cells that may arise indirectly from the experimental manipulation of the cells. For example, transduction of a gene (or genes) into the cells of interest with vectors adds the gene(s) to the cells, but may also change cell behavior in unrelated and unanticipated ways. No permanent record of the endpoint is available. The inability to study the dynamics of cell interactions with the substrate and the impermanence of the endpoint are limitations of this technique.

Cell migration through a membrane. One measure of cell migration currently in use assesses the quantity of cells crossing a membrane under the influence of chemical attractants. The modified "Boyden chamber" assay (Phelps P and Stanislaw D 1969; Jungi T W 1975; Fedun et al U.S. Pat. No. 5,578,492) has afforded many studies of the influence of different compounds, drugs, and reagents on putative cell motility. In this technique, cells are loaded on one side of a membrane; the membrane has pores of a diameter smaller than the diameter of the cells under investigation. Once cells are loaded on one side of the membrane, the chamber is incubated for periods of time. After expiration of that interval the opposite side of the membrane or the opposite chamber is analyzed for the presence of cells that have crossed the membrane. This technique assesses the final condition of the chamber after a biological process has ensued. Experimental manipulations allowed in this system are only possible prior to the start of the study. For example, the cells could be genetically engineered, or the membrane can be pretreated with different substances. Biological processes occurring while the cells transit through the membrane cannot be directly studied since the cells are not accessible. Signal transduction processes in response to the cell's contact with the membrane or other substances cannot be addressed. These assays are attractive for their convenience in set-up, and because the movement of cells through pores has purported geometric analogies to the invasion process in physiological circumstances. However, movement of cells along any path is inherently a one-dimensional act; the cells relocate from point "A" to point "B." Although the route taken may be nonlinear, the moment-by-moment dynamic is one dimensional. The determination of the endpoint of migration in Boyden chambers or modified Boyden chambers is often a consumable measurement (radioactivity counts, cell counts in a hemacytometer; calorimetric staining of cells); this is not a permanent record. Additionally, the volumes of the chambers used for the Boyden chamber assay are such that relatively large amounts of biochemical regents (antibodies, enzyme blocking agents, gene regulatory control factors, etc.) are necessary for treatments in these systems. Because of the cost of many reagents, this is a substantial limitation in this assay. Because factors added to the target chamber may percolate through the membrane pores, and may even coat the linings of the pores, the Boyden chamber may measure response of the cells to soluble (chemotaxis) as well as to insoluble (haptotaxis) factors.

Micro scale monolayer migration assays. One straightforward approach to study of cell movement has been the monolayer "wound" assay (Zetter B R 1980; DiMuzio P J et al 1995) in which a confluent monolayer of cells is scraped, creating an open space or wound in the cell monolayer. As this space is filled in by the remaining cells, cell motility is assessed. Confounding use of this assay is the recognition that as cells are maintained in monolayer conditions, they elaborate an extracellular matrix, which becomes an uncontrollable variable in studies of how different specific matrix proteins influence cell movement. Additionally, mechanical disruption of cell-to-cell connections, caused by the wounding process, may damage the cells in ways difficult to control or address. This assay also suffers from an inability to automate the measurements. Nor does this strategy lend itself to a screening approach to identify factors that influence cell migration.

Independent derivations of monolayer migration assays have recently been reported. In the first, a cell suspension in molten agarose was used to deposit cells in a defined circle on a substrate (Varani J et al 1978; Barak Y et al 1983; Rupnick M A et al 1988; Milner R et al 1997). The distribution of cells that had emigrated from the initial seeding area is visualized by conventional inverted microscopy, and measurements of the distance traveled are made. Microliter volume pipettors enable small areas of initial seeding of cells to be established from which cell migration is monitored. Since the agarose drop is deposited by hand, success in depositing the cells at a precise, predetermined site is variable. Development of an automated measurement process for tracking cell migration would be difficult using this method. Furthermore, different sources of agarose lead to lot-to-lot variations which could impact both the viscosity of the molten agarose leading to inconsistent settling of cells through the medium, as well as the presence of unknown contaminants which could influence cell behavior. Also, experimental treatments with reagents like drugs, antibodies, or antisense oligonucleotides, would need to readily diffuse through the agarose in order to gain access to the migrating cells. This assumption may be spurious. Maintenance of the agarose in a liquid state also requires temperatures of $\geq 42°$ C. which may be difficult to maintain on a substrate while cells are sedimenting out of the agarose. The smaller the drop of agarose, the more rapid the temperature would cool, leading to cells being suspended in the gelled agarose, rather than dropping onto the surface. A warm surface to ensure that the agarose remained liquid would also lead to rapid drying of the agarose, and osmotic changes to the cells. This approach is technically very demanding as far as control of physical variables is concerned.

A reverse approach, the "under agarose migration assay," uses wells cut into a bed of gelled agarose into which cells are deposited for subsequent movement away from the initial site, traveling under the gelled agarose (Nelson R D et al 1975). Physical restraints imposed by cutting or casting wells in agarose lead to use of large areas of deposited cells. Optical distortion imposed by the residing agarose bed, and the inability to use high power optical instruments to assess subcellular structures or antibody-labeled biomolecules, leave this as a simple gross cell movement measurement system.

Recently, Chicione M R and Silbergeld D L (1995) reported modifications in cell seeding strategies using conventional cell culture cloning rings (0.5–0.7 cm diameter) into which cells were seeded as a circle. A mathematical formula was devised with which to chart changes in cell density at different distances from the initial seeded area of cells. The initial seeded area of cells was relatively large (1 $cm^2$), and the volumes of media to support the cells for the duration of the assay also became relatively large. Furthermore, the migrating cells at the perimeter of the sedimented circle of cells comprise a very small fraction of the total cells under these conditions.

Lastly, Berens et al (1994) used custom produced glass sedimenting cylinders cut from micropipettes as the conduit through which to deposit cells as a defined circle. The area was small (1 mm across), and the volumes needed for the assay were on the order of 20–50 microliters. The glass cylinders were, however, unstable, and would easily tip over or slide on the substrate to sites that were away from the intended area and lead to unusable data. Because these glass cylinders were cut from manufactured glass tubing, the bore of the sedimenting chamber would vary significantly from cylinder to cylinder. This raised the variability in initial measurements for the migration assay. The glass cylinders have a wide base, which physically contacts the surface onto which the cells deposit. When the cylinders are removed, the close space between the cylinder and the surface creates a strong capillary force, frequently dislodging the attached cells. Despite these limitations, monolayer migration assays demonstrate the utility of studies of cell movement on flat substrates.

Remaining deficiencies in current methods to deposit cells are: lack of reproducibility, mechanical difficulties in use, limited throughput of experiments for screening new agents, inability to study cell-cell interactions, and only limited potential for video microscopy or computerized data collection.

Additional material pertinent to the physical and biological features of the invention:

Definitions or Clarification of Terms and Concepts
Optics of Conventional Microscopes Living cells can be optically imaged using an inverted microscope. For purposes of this invention, microscopic analysis of sedimented cells is desirable for at least two reasons. The first is to serially (over time) follow the location of individual cells or to measure the radius of a circle circumscribing the peripheral cells (Berens et al 1994). Serial measurements of the radius of the cell population can be achieved using optics of low magnification power in order to image the entire area occupied by cells. Since the area will increase over time, as the cells disperse or migrate from the original site of sedimentation, the area of sedimentation must be smaller than an area which can be seen using a low power objective lens (typically 1000 microns in diameter using a 2.5× objective lens). This indicates that a channel radius of 500 microns is an upper limit of size. A second application is to enumerate cell numbers within preassigned circular areas radiating from the center of the deposited cells (Chicione M R and Silbergeld D L 1995). In cases of cell counting or cell characterization at locations within the population of sedimented cells, an investigator will typically use a high-powered objective lens to best identify, count or characterize individual cells. Such an analysis does not place upper limits on the size of the sedimented population of cells.

Circumference, perimeter, or rim of a circle is the virtual boundary between the round area within which the cells are deposited and the unoccupied surface texture of the surface. For purposes of this discussion, cells at the perimeter, along the circumference, are those with least interference or influence from other cells. The perimeter cells show the most unhindered interaction with the substrate that may influence cell movement. As the radius of the circle of deposited cells increases, the perimeter cells constitute an increasingly small fraction of the whole cell population. Contrastingly, as the radius of the circle of deposited cells gets smaller, the perimeter cells become an increasingly larger component of the entire population of cells. In order to best evaluate cell movement at the periphery, a small circle of cells is most effective.

Sedimentation is a process whereby gravity causes heavier objects in suspension to settle to the lowest part of the system. For purposes of this invention, sedimentation is the process whereby gravity pulls the cells through the standing column of solution that fills the channels in the manifold. The cells sediment onto a defined geometric area defined as the bottom (exit) dimensions of the channel (typically a circle). Forces greater than unit gravity (1×g) may damage cells.

Surface tension (γ). This is a physical property of liquids and solutions. Surface tension of a solution changes with temperature and with the concentrations of solute(s) in the solution. For purposes of this invention, the surface tension of physiological saline solution (in which most cell culture media is prepared) is approximately 72 mN/m (or dynes $cm^{-1}$). The surface tension of a solution determines the capillary force that will cause the solution to move into a small channel. That is, the surface tension defines the physical dimensions of a channel that will hold a volume of liquid for sedimentation of cells onto a specific area. The surface tension relates to the design of this invention by the following formula:

$$\gamma = \tfrac{1}{2} rgph$$

(The other variables are described below.)

Radius of the channel (r) is the geometric distance from the center of the channel to the edge. For purposes of this invention, the radius of the channel in the cell sedimentation manifold is approximately 0.5 mm (0.05 cm), which allows the cells to sediment to a circle of this radius. This area is readily seen using an inverted microscope with a 2.5× or 5.0× objective lens and a 10× ocular lens.

Gravitational force (g) is the attractive force exerted on objects. This is a physical constant of 980.665 cm $sec^{-2}$. This value is used to calculate the dimensions of the channels in the manifold.

Density (ρ) of the solution used to seed and culture the cells is a physical constant of the solution based on the amount and kinds of solutes in that solution. For purposes of this invention, the density of cell culture media ranges from 1.009–1.015 $g/cm^3$. Water has a density of 0.99821 $g/cm^3$ at 20° C.

Height (h) is the distance to which the solution should rise in the channel. For purposes of this invention, the height is a preassigned value based on the intent to have the mass of the cell sedimentation manifold suitable to provide a heat sink for the seeded cells while also being of dimensions that enable ready manual manipulation of the manifold. The height should also be of such a magnitude that the solution can be drawn up to the top of the channel by surface tension, based on the formula shown above.

Heat sink is a pragmatic term referring to the thermal conductivity of the material in which the manifold is made. For the purpose of this invention, stainless steel shows a low thermal conductivity, consequently it holds its temperature against the temperature of the environment. Allowing the cells to sediment at 4° C. suspends biochemical reactions in the cells until the investigator elects to raise the temperature to 37° C. This is readily done by placing the slide into an incubator or onto a warming tray of the desired temperature.

The interdependent relationship between the surface tension (impacting radius and height of the channels in the manifold) and the optics of conventional inverted microscopy (constraining the radius of the sedimented cells) has been accounted for in the design of the channels in the manifold. Additionally, the independence of each of the channels of the manifold has been preserved by the design of the device. This independence allows isolation of each channel and its seeded circle from the fluid in other channels as well as the surfaces under each of the channels where cells are deposited. The device fits precisely over conventional, premasked microscope slides.

OBJECTS AND ADVANTAGES

My invention, the cell sedimentation manifold, is a device for reproducibly depositing living cells onto a prescribed area of a surface with the viability and function of the cells remaining intact.

The invention affords extremely simple loading of cells of many different kinds, making studies of cell migration very easy.

The design of the manifold enables testing for the effects on cell migration of new compounds in very small quantities in a screening mode. Biochemical effects of new compounds on migrating cells can be studied as the cells migrate. Manufacturing cell sedimentation manifolds of a precise configuration allows computer control of experiment execution and data collection. After serial measurements of cell migration, the slides can be processed for a permanent record of outcome. This is a significant advantage over other impermanent, single endpoint assays.

A particularly useful advantage of the cell sedimentation manifold is the ability to study how other cells influence cell migration. The manifold can be used to sediment cells on top of an established cell monolayer of the same or different cell type. The migrating cells can be labeled in such a manner as to subsequently identify them. This labeling can be by use of fluorescent tags, genetic markers, or transduction of an indicator gene. Other applications would include depositing tissue sections onto microscope slides and then using the manifold to place migrating cells onto the sections. In this manner, effects of tissue differences could be studied for their influence on cell migration. This is a novel opportunity afforded by this device.

The ability to deposit cells in a defined location provides an opportunity for video microscopic analysis of the serial motion of cells.

Because the device can be employed to position cells on glass microscope slides, modern imaging instruments such as confocal microscopes and atomic force microscopes can be used to analyze the cells during their migration. Because the cells are established as confluent monolayer within a predetermined area, the peripheral cells can be readily detected to be migrating in an overall net perpendicular direction relative to the rim of the circle, facilitating the assignment of the leading edge of the migrating cells.

Because of the reduced area on which the cells deposit, the fraction of cells able to migrate (those at the rim) is increased over other techniques using larger circles of deposited cells. This is because the circumference of a circle increases in direct proportion to the radius, while the area increases as the square of the radius. Smaller circles have proportionally more rim (migrating) cells than larger circles.

The manifold establishes the cell migration experiment in an "on-line" mode, affording the novel option to temporally manipulate enzymes, biochemicals, or gene expression in the migrating cells; the manipulation can be subsequently washed out of the experiment, affording the cells to regain behavior of the pretreatment state. This allows each cell migration study to serve as its own control experiment; the effect of treatment can be compared to the migration behavior of the cells before and after manipulation.

Because the cell sedimentation manifold is constructed of a dense material, this serves as a cooling chamber by which cell metabolism is largely suppressed. Removal of the cell sedimentation manifold, and placing the slide at 37° C., serves as a start signal for the cellular physiology to become reactivated. This is an advantage in synchronizing the activity of the cells to a standardized time point.

Further objects and advantages of my invention will become apparent from a consideration of the drawings and ensuing description.

Figure 1A:
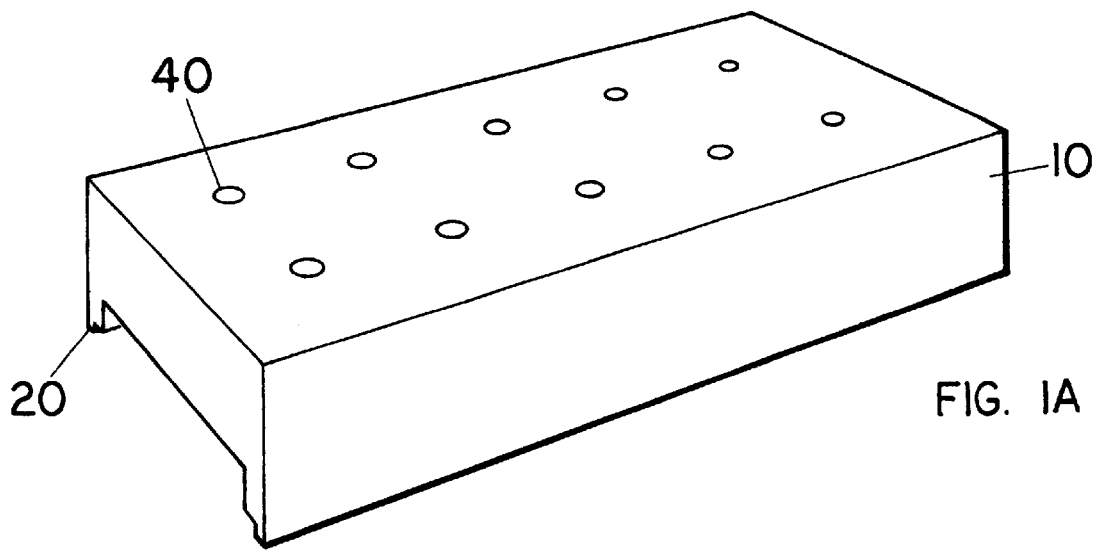
FIG. 1 shows a top oblique view of the cell sedimentation manifold. One or a plurality of channels can be manufactured into the manifold; ten are depicted in this figure.

LIST OF REFERENCE NUMERALS 10 body of cell sedimentation manifold, comprised of steel
20 overhanging tabs on side of manifold
30 longitudinal positioning tab on manifold
40 loading port on top of manifold providing access to sedimenting channel; one of ten
50 exit port from bottom of sedimenting channel; one of ten
60 beveled edge of exit port on bottom of manifold
70 commercially-available microscope slide

SUMMARY OF THE INVENTION

In accordance with the present invention a device comprises a solid block of material having vertical channels at predetermined locations, having tabs that both snugly align said device on a predetermined surface and also suspend the exit ports from the channels at predetermined heights above the surface.

DESCRIPTION OF THE PREFERRED EMBODIMENT—FIGS 1 TO 3

Figure 1B:
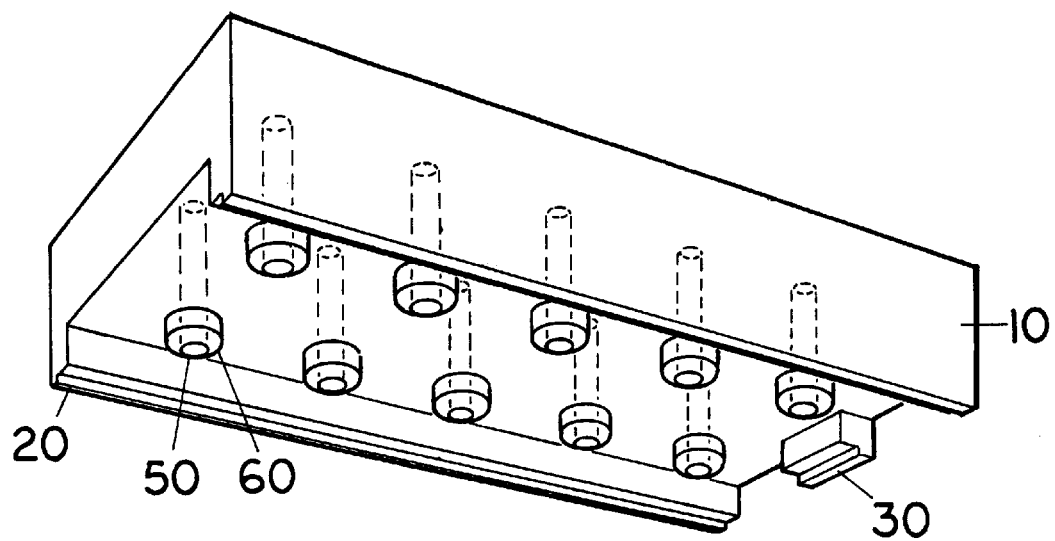
Figure 2A:
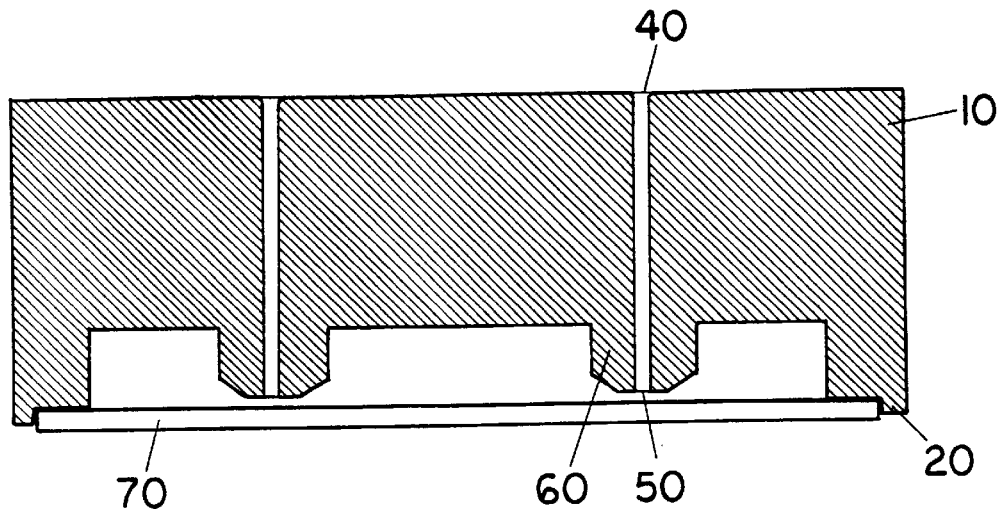
FIG. 2 is an exploded cutaway view of the cell sedimentation manifold; panel 2A highlights the aspects of the device which hold it securely on a microscope slide resulting in the exit ports from the channels residing at the intended height above the slide; panel 2B shows a top oblique view of the cell sedimentation manifold, illustrating longitudinal arrest of the device on the microscope slide by virtue of the end tab.
Figure 2B:
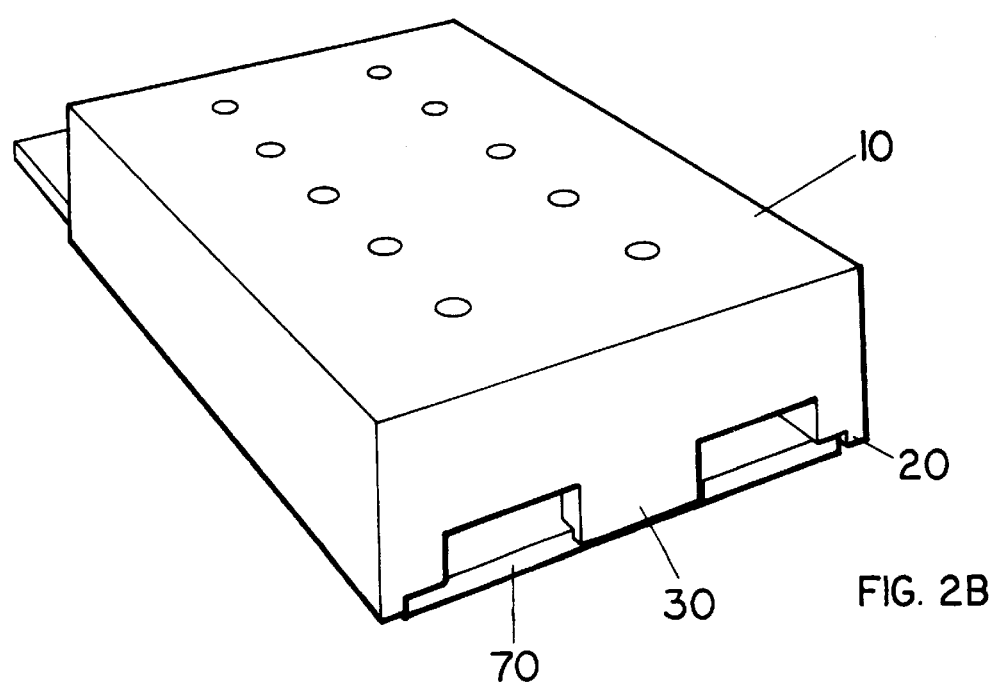

The preferred embodiment of the present invention FIG. 1A (top view) and FIG. 1B (bottom view) is a stainless steel rectangular solid 10 that is slightly larger than the dimensions of a conventional microscope slide 70 (approximately 1 in×4 in). The solid material is stainless steel, which serves as a heat sink to maintain a low temperature, preferably 4° C. Running vertically, at predetermined intervals matched to ten open areas of a commercially-available Teflon-masked slide, are ten channels 40 of 1.0 mm diameter that run from the top 40 to the bottom of the steel block 50 FIG. 2A (cross sectional view through two of the channels). The bottom surface of the manifold is milled along its bottom edges to generate slight overhanging tabs at those edges 20 FIG. 1B (bottom view) and FIG. 2A (cross sectional view) and at one of the ends of the block 30 FIG. 1B (bottom view) and FIG. 2B (oblique view); these serve to stabilize the manifold on the glass slide 70, eliminating lateral and longitudinal shifting during use. The bottom surface of the manifold is further milled to leave the channel exits 50 slightly above the surface onto which the cells sediment FIG. 2A (cross sectional view). The material around the bottom segment of each channel 50 is removed, leaving a virtual 'tube' that exists in isolation from the other channels FIG. 1B (bottom view) and has a bevel 60 FIG. 1B (bottom view) and FIG. 2A (cross sectional view) to reduce capillary force near the exit port of the channel 50 FIG. 2A (cross sectional view). The total height of the manifold is less than 2.5 cm, which is the theoretical limiting distance that surface tension will bring physiological fluid up the channel. Preferably, the height of the manifold is 1.25 cm. The manifold is highly durable and reusable.

From the description above, a number of advantages of my cell sedimentation manifold become evident:

(a) My invention is a device for depositing living cells onto a prescribed area of a surface.

(b) The invention affords extremely simple loading of cells of many different kinds, making studies of cell migration very easy.

(c) The design of the manifold enables testing for the effects on cell migration of new compounds in very small quantities in a screening mode. Biochemical effects of new compounds on migrating cells can be studied as the cells migrate.

(d) Manufacturing cell sedimentation manifolds of a precise configuration allows computer control of experiment execution and data collection.

(e) After serial measurements of cell migration, the slides can be processed for permanent record of outcome. This is a significant advantage over other impermanent, single end-point assays.

(f) A particularly useful advantage of the cell sedimentation manifold is the ability to study how other cells influence cell migration. The manifold can be used to sediment cells on top of an established cell monolayer of the same or different type. The migrating cells can be labeled in such a manner as to subsequently identify them. This labeling can be by use of fluorescent tags, genetic markers, or transfection of an indicator gene. Other applications would include depositing tissue sections onto microscope slides and then using the manifold to place migrating cells onto the sections. In this manner, effects of tissue differences could be studied for their influence on cell migration. This is a novel opportunity afforded by this device.

(g) The ability to deposit cells in a defined location provides an opportunity for video microscopic analysis of the serial motion of cells.

(h) Because the device can be employed to position cells on glass microscope slides, modern imaging instruments such as confocal microscopes and atomic force microscopes can be used to analyze the cells during their migration. Because the cells are established as confluent monolayer within a defined area, the peripheral cells can be readily determined to be migrating perpendicular to the rim of the circle, facilitating the assignment of the leading edge of the migrating cells.

(i) Because of the reduced area on which the cells deposit, the fraction of cells able to migrate (those at the rim) is increased over other techniques using larger circles of deposited cells. This is because the circumference of a circle increases in direct proportion to the radius, while the area increases as the square of the radius. Smaller circles have proportionally more rim (migrating) cells than larger circles.

(j) The manifold establishes the cell migration experiment in an "on-line" mode, affording the novel option to temporally manipulate enzymes, biochemicals, or gene expression in the migrating cells; the manipulation can be subsequently washed out of the experiment, affording the cells to potentially resume behavior of the pretreatment state. This allows each cell migration study to serve as its own control experiment; the effect of treatment can be compared to the migration behavior of the cells before and after manipulation.

(k) Because the cell sedimentation manifold is constructed of a dense material, this serves as a cooling chamber by which cell metabolism is largely suppressed. Removal of the cell sedimentation manifold, and placing the slide at 37° C., serves as a start signal for the cellular physiology to become reactivated. This is an advantage in synchronizing the activity of the cells to a standardized time point.

OPERATION OF INVENTION

Figure 3A:
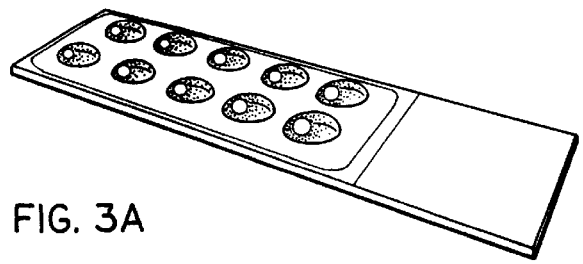
FIG. 3A–3G renders a preferred use of the cell sedimentation manifold, with the five steps involved in use of the device for cell sedimentation.

Step 1. The surface of the microscope onto which the cells will be deposited is treated according to the design of the experiment. Just prior to use of the invention, the teflon-delimited wells on the slide are hydrated in the culture media appropriate to the cells FIG. 3A. Typically, fifty microliters of liquid are deposited onto the well, which forms a bubble on the slide at each well.

Figure 3B:
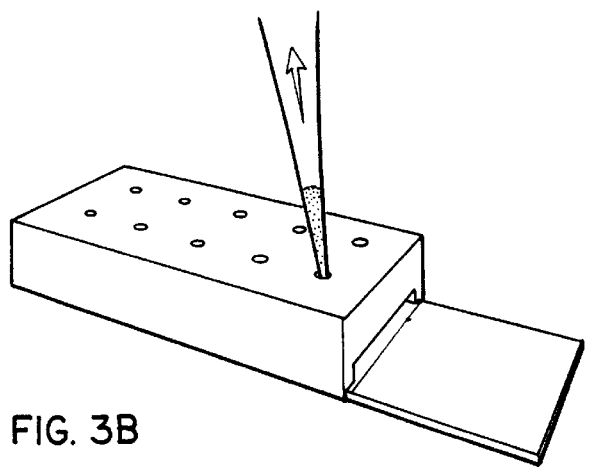
Figure 3C:
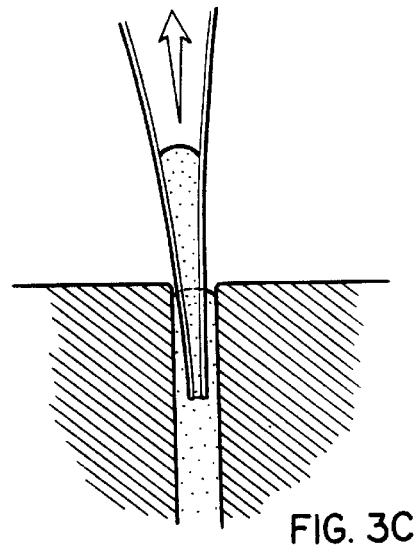

Step 2. The manifold, which has been precooled to 4° C., is gently placed onto the microscope slide, ensuring that the overhanging tabs on side of manifold and the longitudinal positioning tab at the end of the manifold secure the device precisely as intended FIG. 3B. A small aliquot of media, approximately 1 microliter, is aspirated from each channel of the manifold to ensure that no air bubbles reside within the channel FIG. 3C.

Figure 3D:
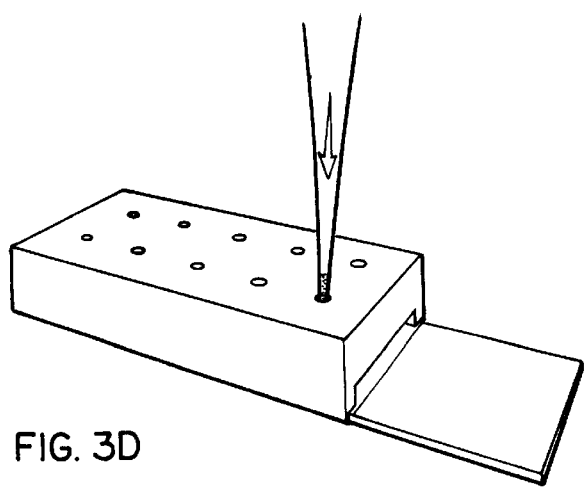
Figure 3E:
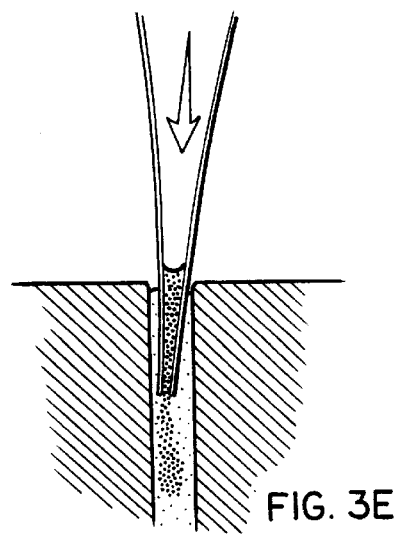

Step 3. The cells are gently deposited into each channel in a volume of one microliter FIG. 3D and FIG. 3E. The numbers of cells deposited varies according to physical characteristics of each cell type being studied. Typically, 500 to 2,000 cells are deposited.

Figure 3F:
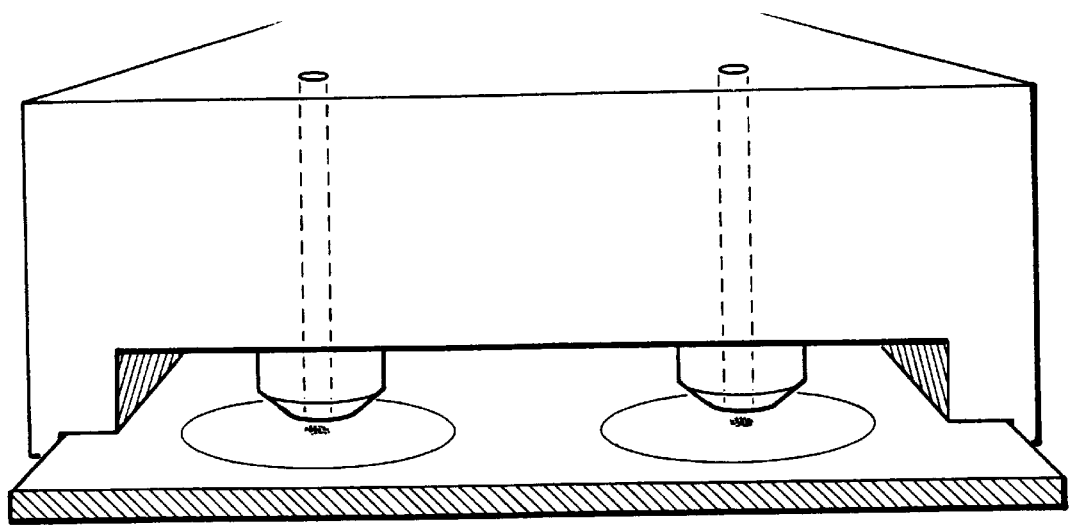

Step 4. The manifold, slide and cells are allowed to stand undisturbed for a set period of time, typically 30 minutes, to allow the cells to sediment FIG. 3F. The manifold, slide and cells are transferred to a controlled temperature and atmosphere incubator (37° C., 5% $CO_2$, humidified air) to allow the cells to attach to the surface of the slide.

Figure 3G:
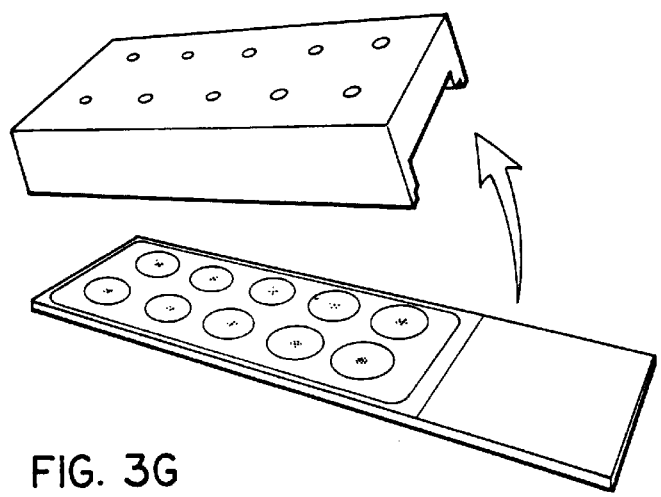

Step 5. The manifold is gently removed from the slide, leaving the cells deposited as a disc of cells at a predetermined location on the slide FIG. 3G.

SUMMARY, RAMIFICATION, AND SCOPE

Accordingly, the reader will see that the cell sedimentation manifold is an invention useful to depositing live cells onto a specified location of a surface. Such deposited cells are convenient and appropriate for conducting studies of how cells move on a specified surface. Each channel of the manifold allows testing or screening for the activity of new drugs, compounds, or other agents on the cells' ability to migrate. Additional advantages of my invention are:

It reproducibly deposits living cells onto a prescribed area of a surface.

It affords extremely simple loading of cells of many different kinds, making studies of cell migration very easy.

It enables testing for the effects on cell migration of new compounds in very small quantities in a screening mode. Biochemical effects of new compounds on migrating cells can be studied as the cells migrate. Manufacturing cell sedimentation manifolds of a precise configuration allows computer control of experiment execution and data collection. After serial measurements of cell migration, the slides can be processed for permanent record of outcome. This is a significant advantage over other impermanent, single endpoint assays.

It provides one skilled in the art the opportunity to study how other cells influence cell migration. It can be used to sediment cells on top of an established cell monolayer of the same or different type. The migrating cells can be labeled in such a manner as to subsequently identify them. This labeling can be by use of fluorescent tags, genetic markers, or transfection of an indicator gene. Other applications would include depositing tissue sections onto microscope slides and then using the manifold to place migrating cells onto the sections. In this manner, effects of tissue differences could be studied for their influence on cell migration. This is a novel opportunity afforded by this device. It gives one the ability to deposit cells in a defined location and thereby provides an opportunity for video microscopic analysis of the serial motion of cells.

It can be employed to position cells on glass microscope slides. Modern imaging instruments such as confocal microscopes and atomic force microscopes can be used to analyze the cells during their migration. Because the cells are established as confluent monolayer within a defined area, the peripheral cells can be readily determined to be migrating in a general net perpendicular direction relative to the rim of the circle, facilitating the assignment of the leading edge of the migrating cells.

It reduces the area over which the cells deposit, and therefore the fraction of cells migrating (those at the rim) is increased over other techniques using larger circles of deposited cells.

It establishes the cell migration experiment in an "on-line" mode, affording the novel option to temporally manipulate enzymes, biochemicals, or gene expression in the migrating cells; the manipulation can be subsequently washed out of the experiment, affording the cells to potentially resume behavior of the pretreatment state. This allows each cell migration study to serve as its own control experiment; the effect of treatment can be compared to the migration behavior of the cells before and after manipulation.

It is constructed of a dense material that holds its temperature, thus serving as a cooling chamber by which cell metabolism is largely suppressed. Removal of the cell sedimentation manifold, and placing the slide at 37° C., serves as a start signal for the cellular physiology to become reactivated. This is an advantage in synchronizing the activity of the cells to a standardized time point.

What is claimed:

1. A method whereby living cells are passively deposited onto a flat surface by sedimentation at unit gravity through culture media-filled vertical channels held within a support which provides a means for stabilizing a predetermined area of said flat surface relative to the position of said channels within the support.

2. The method of claim 1 wherein a plurality of said channels, each having an exit port of the same dimension between 0.1 and 1.0 millimeter diameter, within 20% variance, at the bottom of said channels, establish the size of the said predetermined area of said flat surface onto which the sedimented cells deposit.

3. The method of claim 2 wherein the said plurality of channels are spaced at intervals such that said channels establish reproducible locations of the deposited cells on the said flat surface and that sedimented cells in each area remain separate from cells in adjacent areas.

4. The method of claim 2 wherein said cells sediment through said plurality of channels whose exit ports are suspended at a predetermined, reproducible distance of between 0.1 and 1.0 millimeter above the said flat surface such that the exit port does not contact the flat surface.

5. The method of claim 1 wherein said cells sediment through said channels while being maintained at a cooled temperature whereby the cells' metabolism is suppressed but that the cells remain viable.

6. The method of claim 1 wherein said cells sediment through said channels in a material that can be sterilized, preventing bacterial contamination.

7. The method of claim 1 wherein said cells sediment through channels of a material which is stainless steel.

8. The method of claim 1 wherein the exit ports through which the said cells leave the said channels are milled to a bevel whereby the internal diameter of the exit port is unchanged but the surface tension between the exit port and the said flat surface is reduced.

\* \* \* \* \*